United States Patent [19]

Barnett

[11]  4,048,211
[45]  Sept. 13, 1977

[54] MODIFICATION OF METHADONE SYNTHESIS PROCESS STEP

[75] Inventor: Charles J. Barnett, Indianapolis, Ind.

[73] Assignee: Eli Lilly and Company, Indianapolis, Ind.

[21] Appl. No.: 685,034

[22] Filed: May 10, 1976

[51] Int. Cl.$^2$ .................. C07C 120/00; C07C 121/78
[52] U.S. Cl. ................................................ 260/465 E
[58] Field of Search ................................... 260/465 E

[56] References Cited

U.S. PATENT DOCUMENTS

| | | | |
|---|---|---|---|
| 2,497,739 | 2/1950 | Pfister | 260/465 E |
| 2,540,636 | 2/1951 | Stoughton | 260/465 E |
| 2,574,505 | 11/1951 | Sletzinger et al. | 260/465 E |
| 2,607,794 | 8/1952 | Chamberlin et al. | 260/465 E |

OTHER PUBLICATIONS

Schultz, et al., J.A.C.S., 69 (1947) 2454–2458.
Baizer, Bulletin on Narcotics, U.N. 5 (1), 32–43 (1953).
Cusic, J.A.C.S., 71 (1949) 3546.
Easton, et al., J.A.C.S., 69 (1947) 2941–2942.
Schultz, et al., J.A.C.S., 69 (1947) 188–189.
Cheney, et al., J.A.C.S., 71 (1949) 53–56.

Primary Examiner—Joseph Paul Brust
Assistant Examiner—Robert C. Whittenbaugh
Attorney, Agent, or Firm—James L. Rowe; Everet F. Smith

[57] ABSTRACT

Alkylation of diphenylacetonitrile in methadone synthesis is carried out in presence of sodium hydroxide and DMF.

3 Claims, No Drawings

MODIFICATION OF METHADONE SYNTHESIS PROCESS STEP

BACKGROUND OF THE INVENTION

Methadone, 6-dimethylamino-4,4-diphenyl-3-heptanone, is a synthetic narcotic analgesic developed during World War II by the German chemists, Bockmuhl and Ehrhart, Ann., 561,52 (1948). The synthesis of methandone by their procedure begins with the reaction of diphenylacetonitrile and 1-dimethylamino-2-chloropropane in the presence of sodamide. A high yield of alkylation products is obtained comprising a mixture of two isomeric alkylated diphenylacetonitriles in approximately equal amounts. The nitriles are respectively (I) 2,2-diphenyl-4-dimethylaminovaleronitrile (mp 91°–92° C.) and (II) 2,2-diphenyl-3-methyl-4-dimethylaminobutyronitrile (mp 69°–70° C.). The high melting nitrile, upon reaction with ethyl magnesium bromide and subsequent hydrolysis, yields methadone. The low melting nitrile reacts with ethyl magnesium bromide to give a stable ketimine, 3-imino-4,4-diphenyl-5-methyl-6-dimethylaminohexane, which is hydrolyzed with difficulty to the ketone, isomethadone.

The production of these two isomeric nitriles in a single reaction is explained as follows: In the course of the reaction, 1-dimethylamino-2-chloropropane cyclizes to yield 1,1,2-trimethylaziridinium chloride of the following structure:

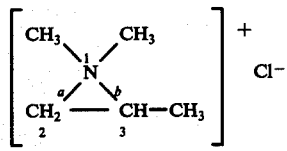

The aziridinium ring is quite unstable and reacts with the diphenylacetonitrile anion (produced under basic conditions) to yield the mixture of isomeric alkylated nitriles set forth above. When the aziridinium ring opens with a breaking of the bond marked with a small a, the desired nitrile I is produced while the rupture of the aziridinium bond marked with a small b yields the isomeric nitrile. Naturally since, on further reaction, nitrile I yields methadone and the nitrile II yields isomethadone, not a useful analgesic, it has been thought desirable to maximize the yields of the desired nitrile I by finding reaction conditions which favored the rupturing of the aziridinium ring at bond a. Many experiments, however, using different solvents, temperatures, etc. yielded, within experimental error, the same ratio of nitrile I and nitrile II, thus leading to the conclusion that the ring opening reaction was a first order reaction and thus independent of environment.

The methadone literature is too voluminous to be reviewed, but the above chemistry is set forth in one or more of the following publications: Schultz et al., J. Am. Chem. Soc., 69, 188,2454 (1947), Cheney et al., ibid, 71, 53, (1949); Easton et al., ibid, 69,2941 (1947), M. M. Baizer, Bull. on Narcotics, U.N. 5 (1), 32 (1953) (a review article). Methadone is referred to as amidon in some of the above publications.

The only reference to a procedure other than the sodamide-toluene or t-butoxide--t-butanol solvent procedures of the above references for the alkylation of diphenylacetonitrile is Cusic, J. Am. Chem. Soc., 71, 3546 (1949). Cusic employed a melt with 1-dimethylamino-2-chloropropane, diphenylacetonitrile and sodium hydroxide in the absence of a solvent. In my hands, both the Cusic and Bockmuhl procedures yield at best a 6:4 isomer ratio of the desired isomer to the undesired (isomethandone intermediate) isomer.

It is an object of this invention to provide an alkylation step in a procedure for the preparation of methadone involving the reaction of 1-dimethylamino-2-chloropropane and diphenylacetonitrile such that the ratio of the desired to undesired isomer is greater than 6:4.

SUMMARY OF THE INVENTION

In accordance with the above and other objects, this invention provides a process whereby 1-dimethylamino-2-chloropropane is reacted with diphenylacetonitrile in the presence of sodium hydroxide in a polar, aprotic solvent. The product of this reaction is a mixture of 2,2-diphenyl-4-dimethylaminovaleronitrile and 2,2-diphenyl-3-methyl4-dimethylaminobutyronitrile in better tha a 6:4 ratio. My novel process is carried out as follows: About a 50–100% molar excess of solid sodium hydroxide is ground to a fine powder and the powder added to a polar, aprotic solvent such as dimethylformamide in, for example, a 1:8 w/v ratio. A solution of diphenylacetonitrile in the same solvent in about a 1:1 or 1:2 w/v ratio is added thereto. After stirring this reaction mixture briefly in order to assure complete formation of the sodium salt of diphenylacetonitrile, a solution of 1-dimethylamino-2-chlorpropane free base is added in increments. The reaction is exothermic and the rate of addition of the free base is such that the reaction temperature can readily be controlled with the cooling means available. The reaction mixture is then heated to about 50° C. for a period of from 1 to 2 hours. The reaction mixture is next cooled, diluted with water, and the resulting suspension extracted several times with a water immiscible solvent, preferably benzene. The organic extracts are combined, washed with water and with saturated sodium chloride and are then dried. Removal of the solvent in vacuo yields a crude product which contains 2,2-diphenyl-4-dimethylaminovaleronitrile and 2,2-diphenyl-3-methyl-4-dimethylaminobutyronitrile in a 2:1 ratio or better as determined by vapor phase chromatography. The isomer mixture is about 90–98 percent of the total weight of isolated product, the remainder being recovered diphenylacetonitrile. The isomer mixture is separated into its component parts by standard procedures such as crystallization from hexane or by chromatography using, for example, silica gel and a benzene-methanol 8:2 solvent mixture as the eluting solvent.

In the above reaction, the reactant concentrations do not affect the isomer ratio, but they do affect the amount of desired isomer obtained in pure state. Obviously, the more complete the reaction of diphenylacetonitrile, the less of that starting material will be present in the nitrile isomer mixture to hinder separation and purification of the separated isomers. We, therefore, prefer to employ a 50–100 percent excess of base and a 10–20 percent excess of 1-dimethyamino-2-chloropropane.

The temperature of the reaction also does not materially influence the isomer ratio but is important to the completeness of the reaction. Temperatures from 35–100 degrees C. are fully operative, but I prefer to carry out my novel reactions at a temperature of about 75° C. with a range of 5° C. (70°–80° C.) being consistent with virtually complete reaction of the diphenylacetonitrile and minimal quantities of by-products.

As previously stated, a polar, aprotic solvent should be used in the above process step. I have found that polar, aprotic solvents having a di-electric constant higher than 28 (when determined at 25° C.) are suitable solvents for the above reaction. Such solvents include dimethylformamide (DMF) $\epsilon_{25}$. 36.71, dimethylacetamide (DMAC) $\epsilon_{25}$. 37.8, dimethylsulfoxide (DMSO), $\epsilon_{25}$. 45 and other similar solvents including nitrobenzene, N-methyl formamide and hexamethylphosphoramide. It is also important that the polar, aprotic solvent employed as a reaction medium be inert; i.e., not contain any groups which might react either with sodium hydroxide, with chlorpropylamine or with its aziridinium halide intermediate form.

This invention is further illustrated by the following specific examples.

EXAMPLE 1

Following the procedure of Schultz and Sprague, J. Am. Chem. Soc., 70, 48 (1948), a solution containing 3.77 g. of 1-dimethylamino-2-propanol and 10 ml. of chloroform was cooled with stirring to a temperature of about 0° C. A solution of 5.72 g. of freshly distilled thionylchloride in 2 ml. of chloroform was added thereto. The reaction mixture was allowed to come to ambient temperature over a period of about 30 minutes and was then heated to refluxing temperature for an additional 30 minutes. The precipitated material redissolved on heating. 1-Dimethylamino-2-chloropropane hydrochloride began to crystallize from the boiling solvent. The reaction mixture was cooled, diluted with ether and filtered. The reaction product comprising 1-dimethylamino-2-chloropropane hydrochloride weighed about 5.5 g. (95 percent yield). Recrystallization yielded purified 1-dimethylamino-2-chloropropane hydrochloride melting at 192°–193° C.

Two and two tenths grams of 1-dimethylamino-2-chloropropane hydrochloride were dissolved in an equal volume of water to which was added 1.5 ml. of 20 percent aqueous sodium hydroxide. The mixture was thoroughly shaken. 1-Dimethylamino-2-chloropropane free base, being insoluble in the aqueous alkaline solution, separated and the separated amine was extracted with two 5 ml. portions of ether. The ether layers were combined and dried. Removal of the ether in vacuo yielded as an oily residue 0.8 g. of 1-dimethylamino-2-chloropropane.

A suspension of 1.36 g. (0.034 mol.) of finely ground sodium hydroxide was prepared in 10 ml. of dried DMF. A solution containing 6.0 g. (0.031 mol.) of diphenylacetonitrile in 8 ml. of DMF was added thereto at room temperature. After stirring the mixture for 15 minutes, 4.1 g. (0.034 mol.) of 1-dimethylamino-2-chloropropane were added. The reaction mixture was heated with stirring to about 50° C. for about 1.5 hours and was then cooled. The cooled reaction mixture was diluted with an equal volume of water and the resulting suspension, containing a mixture of 2,2-diphenyl-4-dimethylaminovaleronitrile and 2,2-diphenyl-3-methyl-4-dimethylaminobutyronitrile formed in the above reaction, was extracted with two 350 ml. portions of benzene. The benzene extracts were combined, washed with water and with saturated sodium chloride solution and then dried. Removal of the solvent yielded about 7.83 g. of the crude reaction product which was shown by vapor phase chromatography to contain 58.4 percent, 2,2-diphenyl-4-dimethyl-aminovaleronitrile, 29.3 percent of 2,2-diphenyl-3-methyl-4-dimethylaminobutyronitrile, and 10.8 percent of starting material diphenylacetonitrile. The methadone intermediate isomers were thus present in a ratio of 66.5: 33.5 Recrystallization of the crude reaction product from hexane yielded purified 2,2-diphenyl-4-dimethylaminovaleronitrile which can be converted to methadone by the procedure of Bockmuhl and Ehrhart, Ann., 561,52 (1948). In this procedure, the valeronitrile is reacted with ethyl magnesium bromide to yield an intermediate imine which is hydrolized with base to yield the corresponding ketone.

The above reaction was also carried out employing DMSO in place of DMF as a solvent. The crude product analyzed for 60.6 percent of the desired valeronitrile isomer, 31.2 percent of the undesired methyl butyronitrile isomer, and 3.4 percent of unreacted diphenylacetonitrile (isomer ratio 66:34).

EXAMPLE 2

A solution of 19.3 g. (0.1 mol.) of diphenylacetonitrile in 60 ml. dimethylformamide was added with stirring to a slurry of 8 g. (0.2 mol.) finely ground sodium hydroxide in 40 ml. dimethylformamide under nitrogen. The dark red color of the nitrile anion was observed immediately. The mixture was heated to 75° ± 5° C. and 14.85 g. (0.12 mol.) 1-dimethylamino-2-chloropropane were added at a rate such that the reaction temperature was maintained in the range 75°–80° C. with external cooling when necessary. The reaction mixture was stirred at 75° C. under nitrogen for 1 hour, cooled and diluted with 250 ml. water. The aqueous mixture was extracted with 400 ml. of benzene in three portions. The extracts were combined and the combined extracts were washed with water and with saturated sodium chloride solution, and were then dried over anhydrous sodium sulfate. Removal of the benzene at reduced pressure afforded 26.7 g. of the crude mixture of isomeric nitriles, shown by VPC analysis to contain 64.8 percent 2,2-diphenyl-4-dimethylamino valeronitrile, 34.0 percent 2,2-diphenyl-3-methyl-4-dimethylaminobutyronitrile, and 0.35 percent unreacted diphenylacetonitrile, the remainder of the material consisting of unidentified volatile impurities. The reaction was thus 99.6 percent complete. The ratio of isomeric nitriles was therefore, 65.6: 34.4 in favor of the desired valeronitrile methadone intermediate. The crude product thus obtained was allowed to crystallize from hexane, affording 12.6 g. (45 percent of theory based on diphenylacetonitrile) of 2,2-diphenyl-4-dimethylaminovaleronitrile, mp 90°–91° C. having a purity of 99 percent by VPC analysis.

As previously stated, the produce of my novel process step is an intermediate in the synthesis of methadone. Methadone is not only a useful analgesic in its own right, but has recently proven to be of considerable value in substituting for heroin in heroin addiction. Methadone substitution allows the usual heroin addict to lead a more nearly normal life even though an addiction to methadone is substituted for the addict's present heroin addiction.

I claim:

1. In a process for preparing a mixture of 2,2-diphenyl-4-dimethylaminovaleronitrile and 2,2-diphenyl-3-methyl-4-dimethylaminobutyronitrile by the reaction of diphenylacetonitrile and 1-dimethylamino-2-chloropropane, the improvement which consists in carrying out the reaction in an inert polar, aprotic solvent having a dielectric constant greater than 28 at 25° C. by forming the sodium salt of diphenylacetonitrile with sodium hydroxide and then adding thereto 1-dimethylamino-2-chloropropane.

2. A process according to claim 1 in which the inert polar, aprotic solvent is a member of the group consisting of N,N-dimethylformamide, N-methylformamide, di-methylsulfoxide and dimetjhylacetamide.

3. A process according to claim 1 in which the inert polar, aprotic solvent is dimethylformamide.

* * * * *